US 10,646,266 B2

(12) United States Patent
Smith et al.

(10) Patent No.: US 10,646,266 B2
(45) Date of Patent: May 12, 2020

(54) SYSTEM AND METHOD FOR RETURN ELECTRODE MONITORING (71) Applicant: COVIDIEN LP, Mansfield, MA (US)

(72) Inventors: Robert B. Smith, Loveland, CO (US); Steven C. Rupp, Arvada, CO (US); Daniel A. Friedrichs, Aurora, CO (US)

(73) Assignee: COVIDIEN LP, Mansfield, MA (US)

( * ) Notice: Subject to any disclaimer, the term of this patent is extended or adjusted under 35 U.S.C. 154(b) by 690 days.

(21) Appl. No.: 15/340,150

(22) Filed: Nov. 1, 2016

(65) Prior Publication Data
US 2017/0135744 A1 May 18, 2017

Related U.S. Application Data (60) Provisional application No. 62/259,450, filed on Nov. 24, 2015, provisional application No. 62/255,087, filed on Nov. 13, 2015.

(51) Int. Cl.
A61B 18/12 (2006.01)
A61B 18/00 (2006.01)
A61B 18/16 (2006.01)

(52) U.S. Cl.
CPC .......... A61B 18/1233 (2013.01); A61B 18/16 (2013.01); A61B 2018/00577 (2013.01);
(Continued)

(58) Field of Classification Search
CPC ................ A61B 18/1233; A61B 18/16; A61B 2018/1286; A61B 2018/165;
(Continued)

(56) References Cited

U.S. PATENT DOCUMENTS 4,231,372 A 11/1980 Newton
4,416,276 A 11/1983 Newton et al.
(Continued)

FOREIGN PATENT DOCUMENTS

EP 2283788 A1 2/2011

OTHER PUBLICATIONS

European Search Report dated Apr. 11, 2017 in corresponding European Patent Application No. 16198322, 7 pages.

Primary Examiner — Eun Hwa Kim
Assistant Examiner — Christine A Dedoulis
(74) Attorney, Agent, or Firm — Carter, DeLuca & Farrell LLP (57) ABSTRACT A system and method for return electrode monitoring are provided. The system includes an isolation circuit, a first controller, a second controller, and a detection circuit. The isolation circuit includes a transformer having a primary winding and a secondary winding. The first controller is coupled to the primary winding. The second controller and the detection circuit are coupled to the secondary winding. The detection circuit includes an interrogation signal circuit, a resonant tank filter, and a current-to-voltage converter. The interrogation signal circuit provides an interrogation signal to at least one electrode pad. The resonant tank filter filters a response signal received from the electrode pad. The current-to-voltage converter generates a voltage signal based on a current value of the response signal. The second controller generates a digital impedance value based on the voltage signal, and provides the digital impedance value to the first controller by way of the isolation circuit.

20 Claims, 5 Drawing Sheets (52) U.S. Cl.
CPC .......... *A61B 2018/00589* (2013.01); *A61B 2018/00595* (2013.01); *A61B 2018/00601* (2013.01); *A61B 2018/00642* (2013.01); *A61B 2018/00708* (2013.01); *A61B 2018/00779* (2013.01); *A61B 2018/00875* (2013.01); *A61B 2018/00892* (2013.01); *A61B 2018/00988* (2013.01); *A61B 2018/1286* (2013.01); *A61B 2018/167* (2013.01)

(58) Field of Classification Search
CPC .... A61B 2018/167; A61B 2018/00875; A61B 2018/00779; A61B 2018/00708; A61B 2018/00595; A61B 2018/00577; A61B 2018/00601; A61B 2018/00589; A61B 2018/00642; A61B 2018/00892; A61B 2018/00988
USPC ........................................................ 606/35
See application file for complete search history.

(56) References Cited

U.S. PATENT DOCUMENTS

| | | | |
|---|---|---|---|
| 4,416,277 | A | 11/1983 | Newton et al. |
| 4,848,335 | A | 7/1989 | Manes |
| 5,695,494 | A | 12/1997 | Becker |
| 6,565,559 | B2 | 5/2003 | Eggleston |
| 7,160,293 | B2 | 1/2007 | Sturm et al. |
| 8,187,263 | B2 | 5/2012 | Behnke et al. |
| 2001/0031962 | A1 | 10/2001 | Eggleston |
| 2006/0079872 | A1 | 4/2006 | Eggleston |
| 2007/0073284 | A1 | 3/2007 | Sturm et al. |
| 2009/0198230 | A1* | 8/2009 | Behnke ............. A61B 18/1233 606/35 |
| 2010/0217259 | A1* | 8/2010 | Strauss ............. A61B 18/1233 606/38 |
| 2010/0241023 | A1 | 9/2010 | Gilbert |
| 2014/0094796 | A1* | 4/2014 | Behnke, II ......... A61B 18/1233 606/35 |

* cited by examiner

SYSTEM AND METHOD FOR RETURN ELECTRODE MONITORING

CROSS-REFERENCE TO RELATED APPLICATIONS

The present application claims the benefit of and priority to U.S. Provisional Application Ser. No. 62/259,450, filed on Nov. 24, 2015, and U.S. Provisional Application Ser. No. 62/255,087, filed on Nov. 13, 2015, the entire contents of which are incorporated herein by reference.

TECHNICAL FIELD

The present disclosure relates to electrosurgical systems and methods. More particularly, the present disclosure is directed to electrosurgical systems and methods for return electrode monitoring, including monitoring the quality of contact between return electrode pads and the patient during electrosurgical procedures.

BACKGROUND

Energy-based tissue treatment is well-known in the art. Various types of energy (such as electrical, ultrasonic, microwave, cryogenic, heat, laser, and/or the like) are applied to tissue to achieve a desired result. Electrosurgery involves application of high radio frequency electrical current to a surgical site to cut, ablate, coagulate, or seal tissue. Energy-based surgical devices typically include an isolation boundary between the patient and the energy source to isolate the patient from the potentially dangerous voltage and/or current levels. In monopolar electrosurgery, the active electrode is typically part of the surgical instrument held by the surgeon and applied to the tissue to be treated. One or more patient return electrodes are placed remotely from the active electrode to carry the current back to the generator and safely disperse current applied by the active electrode. The return electrodes usually have a large patient contact surface area to minimize heating at that site. Heating is caused by high current densities which directly depend on the surface area. A larger surface contact area results in lower localized heat intensity. Return electrodes are typically sized based on assumptions of the maximum current utilized during a particular surgical procedure and the duty cycle (i.e., the percentage of time the generator is on).

Early types of return electrodes were formed as large metal plates covered with conductive jelly. Later, adhesive electrodes were developed with a single metal foil covered with conductive jelly or conductive adhesive. However, one challenge that arises from employing adhesive electrodes is that, if a portion of an adhesive electrode peels from the patient, the contact area of the electrode with the patient decreases, thereby increasing the current density at the adhered portion and, in turn, increasing the heating of the tissue at that location. This risks burning the patient in the area under the adhered portion of the return electrode if the tissue is heated beyond the point where circulation of blood can sufficiently cool the skin.

To address this problem various return electrode monitoring systems, generically called Return Electrode Contact Quality Monitors (RECQMs) or simply Return Electrode Monitors (REMs), have been developed. Such systems rely on measuring impedance at the return electrode to calculate a variety of tissue and/or electrode properties. These systems detect electrode peeling by identifying changes in amplitude of the impedance of the return electrodes. Prior REM systems, however, require expensive off-the-shelf and custom components that can be heavy and consume a relatively large amount of printed circuit board (PCB) area. Prior REM systems and methods also do not facilitate the measurement of an individual impedance of an interface between a patient and a single pad of a multiple-pad return electrode (such as a split-pad return electrode, for example), and/or the relative impedances of the respective interfaces between the patient and two or more respective pads of a multiple-pad return electrode.

In view of the above, there is a need for an improved system and method for return electrode monitoring that addresses the foregoing challenges and is able to communicate information across the isolation boundary between the energy source and the patient.

SUMMARY

According to an aspect of the present disclosure, a return electrode monitoring system is provided that includes an isolation circuit, a first controller, a second controller, and a detection circuit. The isolation circuit includes a transformer having a primary winding and a secondary winding. The first controller is coupled to the primary winding, and the second controller is coupled to the secondary winding. The detection circuit is coupled to the second controller and to a pair of split electrode pads of a return electrode. The detection circuit includes an interrogation signal circuit, a resonant tank filter, and a current-to-voltage converter. The interrogation signal circuit provides an interrogation signal to at least one of the split electrode pads. The resonant tank filter filters a response signal received from the at least one of the split electrode pads. The current-to-voltage converter generates a voltage signal based on a current value of the response signal. The second controller generates a digital impedance value based on the voltage signal, and provides the digital impedance value to the first controller by way of the isolation circuit.

In another aspect of the present disclosure, the isolation circuit further includes a modulator configured to modulate the digital impedance value according to a predetermined type of modulation and communicate the modulated digital impedance value to the first controller by way of the transformer. The predetermined type of modulation includes, in one example, amplitude modulation and/or phase shift keying modulation.

In still another aspect of the present disclosure, the resonant tank filter is tuned to resonate at a predetermined frequency.

In another aspect of the present disclosure, the second controller is further configured to periodically generate respective digital impedance values based on respective values of the voltage signal successively received at a predetermined time interval, and provide the respective digital impedance values to the first controller by way of the isolation circuit.

In another aspect of the present disclosure, the first controller is configured to receive the digital impedance value and disable delivery of energy to an active electrode of an electrosurgical instrument based on the received digital impedance value.

In another aspect of the present disclosure, the second controller is configured to generate the digital impedance value based on a collective impedance of an interface between a patient and all of the electrode pads of the return electrode.

In another aspect of the present disclosure, the second controller is configured to generate the digital impedance value based on relative impedances of respective interfaces between the patient and the electrode pads of the return electrode.

In another aspect of the present disclosure, the interrogation signal is based on one or more control signals provided to the interrogation signal circuit by the second controller.

In another aspect of the present disclosure, the interrogation signal circuit includes a current limiting network that limits a value of current of the interrogation signal.

According to another aspect of the present disclosure, a method for return electrode monitoring is provided. The method includes generating an interrogation signal, providing the interrogation signal to at least one of a pair of split electrode pads of a return electrode, filtering a response signal received from the at least one of the split electrode pads, generating a voltage signal based on a current value of the response signal, generating a digital impedance value based on the voltage signal, and providing the digital impedance value to a first controller by way of an isolation circuit.

In another aspect of the present disclosure, the method further includes modulating the digital impedance value according to a predetermined type of modulation and communicating the modulated digital impedance value to the first controller by way of a transformer included in the isolation circuit.

In still another aspect of the present disclosure, the predetermined type of modulation includes amplitude modulation and/or phase shift keying modulation.

In another aspect of the present disclosure, the filtering of the response signal is performed by way of a resonant tank filter that is tuned to resonate at a predetermined frequency.

In another aspect of the present disclosure, the method further includes periodically generating respective digital impedance values based on respective values of the voltage signal successively received at a predetermined time interval, and providing the respective digital impedance values to the first controller by way of the isolation circuit.

In another aspect of the present disclosure, the method further includes disabling delivery of energy to an active electrode of an electrosurgical instrument based on the digital impedance value.

In another aspect of the present disclosure, the generating of the digital impedance value includes generating the digital impedance value based on a collective impedance of an interface between a patient and all electrode pads of a split-pad return electrode.

In another aspect of the present disclosure, the generating of the digital impedance value includes generating the digital impedance value based on relative impedances of respective interfaces between a patient and a plurality of respective electrode pads of the return electrode.

In another aspect of the present disclosure, the interrogation signal is based on one or more control signals provided to the interrogation signal circuit by the second controller.

In another aspect of the present disclosure, the interrogation signal circuit includes a current limiting network that limits a value of current of the interrogation signal.

BRIEF DESCRIPTION OF THE DRAWINGS

The above and other aspects, features, and advantages of the present disclosure will become more apparent in light of the following detailed description when taken in conjunction with the accompanying drawings, in which.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Return electrode monitoring ("REM") circuitry in an electrosurgical generator monitors contact area between the patient and one or more return electrode pads. The circuitry prevents tissue damage caused by pad burns due to poor pad contact. The REM circuitry forms a resonant system with the split electrode pads of the return electrode pads which are designed to resonate at a specific interrogation frequency. The REM circuitry detects a signal in response to a supplied drive signal at a predetermined clock frequency (for example, from a controller). The REM circuitry thereafter produces a voltage indicative of the amplitude (for example, magnitude) of the waveform indicative of the resonations. As the impedance between the split pads changes, the resonance of the REM circuit changes as well, this causes the amplitude to change. Thus, by monitoring the changes in the amplitude, the REM circuit determines the magnitude of the impedance between the split pads which is indicative of adherence of the return electrode pad to the patient.

Figure 1:
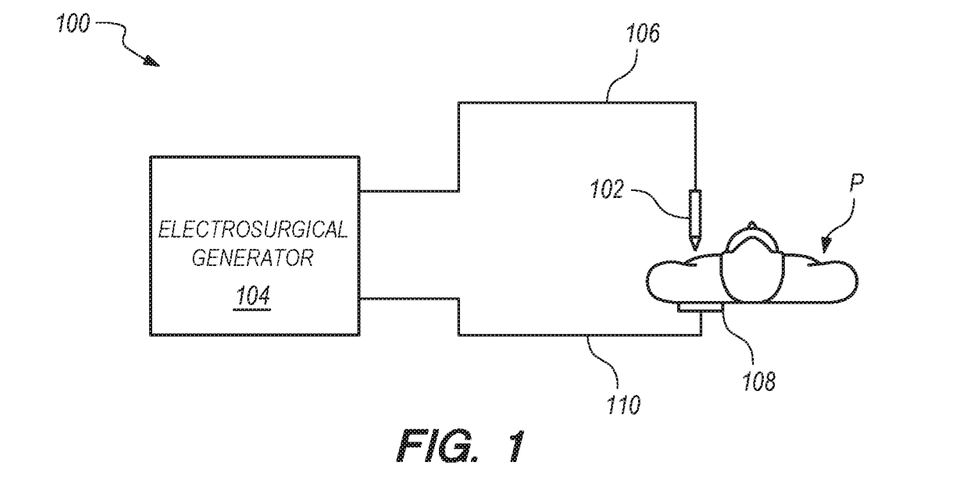
FIG. 1 is a block diagram of an electrosurgical system according to the present disclosure.

FIG. 1 is a block diagram of an electrosurgical system 100 according to one embodiment of the present disclosure. The system 100 includes an electrosurgical instrument 102 having one or more active electrodes for treating tissue of a patient P. The instrument 102 is a monopolar instrument including one or more active electrodes (such as, for example, an electrosurgical cutting probe, ablation electrode (s), and/or the like). Electrosurgical RF energy is supplied to the instrument 102 by a generator 104 via an electrosurgical cable 106, which is connected to an active output terminal, allowing the instrument 102 to coagulate, ablate and/or otherwise treat tissue. Although the generator 104 is described herein as delivering RF energy, this is by example only and not limitation. The generator 104 in various embodiments may additionally or alternatively deliver any type of energy, such as ultrasonic energy, energy of other portions on the electromagnetic spectrum, and/or the like. The energy is returned to the generator 104 through a return electrode 108 via a return cable 110. The system 100 may include a plurality of return electrodes 108 that are arranged to minimize the chances of tissue damage by maximizing the overall contact area with the patient P. In addition, the generator 104 and the return electrode 108 may be configured for monitoring so-called "tissue-to-patient" contact to insure that sufficient contact exists therebetween to further minimize chances of tissue damage.

The generator 104 includes input controls (for example, buttons, activators, switches, touch screen, etc.) for controlling the generator 104. In addition, the generator 104 may include one or more display screens for providing the user with variety of output information (for example, intensity settings, treatment complete indicators, etc.). The controls allow the user to adjust power of the RF energy, waveform, and other parameters to achieve the desired waveform suitable for a particular task (for example, coagulating, cauterizing, intensity setting, etc.). The instrument 102 may also include a plurality of input controls that may be redundant with certain input controls of the generator 104. Placing the input controls at the instrument 102 allows for easier and faster modification of RF energy parameters during the surgical procedure without requiring interaction with the generator 104.

Figure 2:
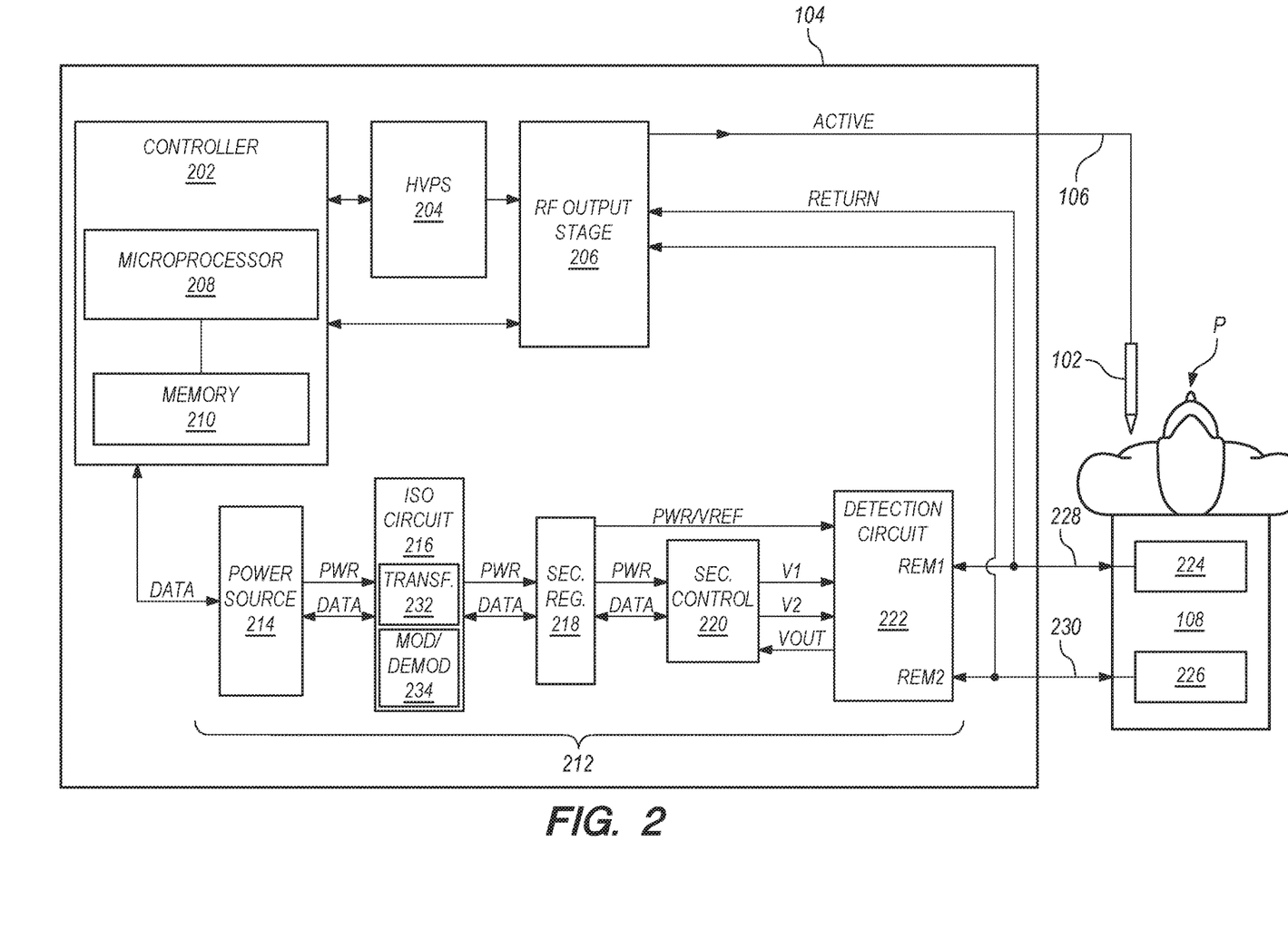
FIG. 2 is a block diagram that shows aspects of an electrosurgical generator according to the present disclosure.

Having described the electrosurgical system 100, reference will now be made to the block diagram of FIG. 2, which illustrates additional aspects of the generator 104 according to the present disclosure. The generator 104 includes a first controller 202, a high voltage DC power supply 204 ("HVPS") and an RF output stage 206. The HVPS 204 provides high voltage DC power to an RF output stage 206, which then converts high voltage DC power into RF energy and delivers the RF energy to the active electrode. In particular, the RF output stage 206 generates sinusoidal waveforms of high RF energy. The RF output stage 206 is configured to generate a plurality of waveforms having various duty cycles, peak voltages, crest factors, and other suitable parameters. Certain types of waveforms are suitable for specific electrosurgical modes. For instance, the RF output stage 206 generates a 100% duty cycle sinusoidal waveform in cut mode, which is best suited for ablating, fusing, and dissecting tissue, and a 1-25% duty cycle waveform in coagulation mode, which is best used for cauterizing tissue to stop bleeding.

The first controller 202 includes a microprocessor 208 operably connected to a memory 210, which may be volatile type memory (for example, random access memory or RAM) and/or non-volatile type memory (for example, flash media, disk media, etc.). The microprocessor 208 includes an output port that is operably connected to the HVPS 204 and/or RF output stage 206 that allows the microprocessor 208 to control the output of the generator 104 according to either open and/or closed control loop schemes. Those skilled in the art will appreciate that the microprocessor 208 may be substituted by any logic processor (for example, control circuit) adapted to perform the calculations discussed herein.

The generator 104 also includes a return electrode monitoring (REM) system 212 having a power source 214, an isolation circuit 216, a secondary regulator circuit 218, a second controller 220, and a detection circuit 222. The topology of the system 212, which is described in further detail below, can operate by using less than 10 watts of isolated power and a data transfer link of less than 10 kilobits per second to transfer control and pad information across the isolation boundary.

The isolation circuit 216, in some examples, includes an isolation transformer 232 and one or more modulators and/or demodulators 234. The isolation transformer 232 is configured to isolate the patient P from one or more power sources (for example, the power source 214, the power source 204, and/or other power sources) of the generator 104. In particular, the isolation transformer 232 includes a primary winding and a secondary winding, with the one or more power sources and the controller 202 coupled to the primary winding and the patient P coupled to the secondary winding (by way of intermediate components including the detection circuit 222, the second controller 220, and the secondary regulator circuit 218, as depicted in FIG. 2). In one example, the one or more modulators and/or demodulators 234 are included on both the primary side of the transformer 232 (for example, coupled to the primary winding) and the secondary side of the transformer 232 (for example, coupled to the secondary winding) and are configured to modulate data and/or demodulate data, respectively, according to one or more predetermined types of modulation and/or demodulation (such as, for example, amplitude modulation (AM) and/or phase shift keying (PSK) modulation), to facilitate the bi-directional communication of data (together with power from the power source 214) across the transformer 232. In one example, a first type of modulation (for instance, AM) is employed to communicate data in a first direction and a second type of modulation (for instance, PSK) that does not interfere with the first type of modulation is employed to communicate data in a second direction, opposite the first direction. Additional details regarding an example implementation of an isolation circuit are described in U.S. Patent Application Publication No. 2015/0088115, which is hereby incorporated by reference herein in its entirety.

The detection circuit 222 is coupled to a pair of split return electrode pads—a first return electrode pad 224 and a second return electrode pad 226 disposed within the return electrode 108. The return electrode 108 is in contact with the patient P and returns the electrosurgical energy to the generator 104 by way of the first and second electrode pads 224 and 226 that are coupled to leads 228 and 230, respectively. In one embodiment, the return electrode 108 may include a plurality of pairs of split electrode pads which are coupled to a corresponding number of leads. The leads 228 and 230 are enclosed in a return cable and are coupled to the RF output stage 206 and to the detection circuit 222 for return electrode monitoring.

Figure 3:
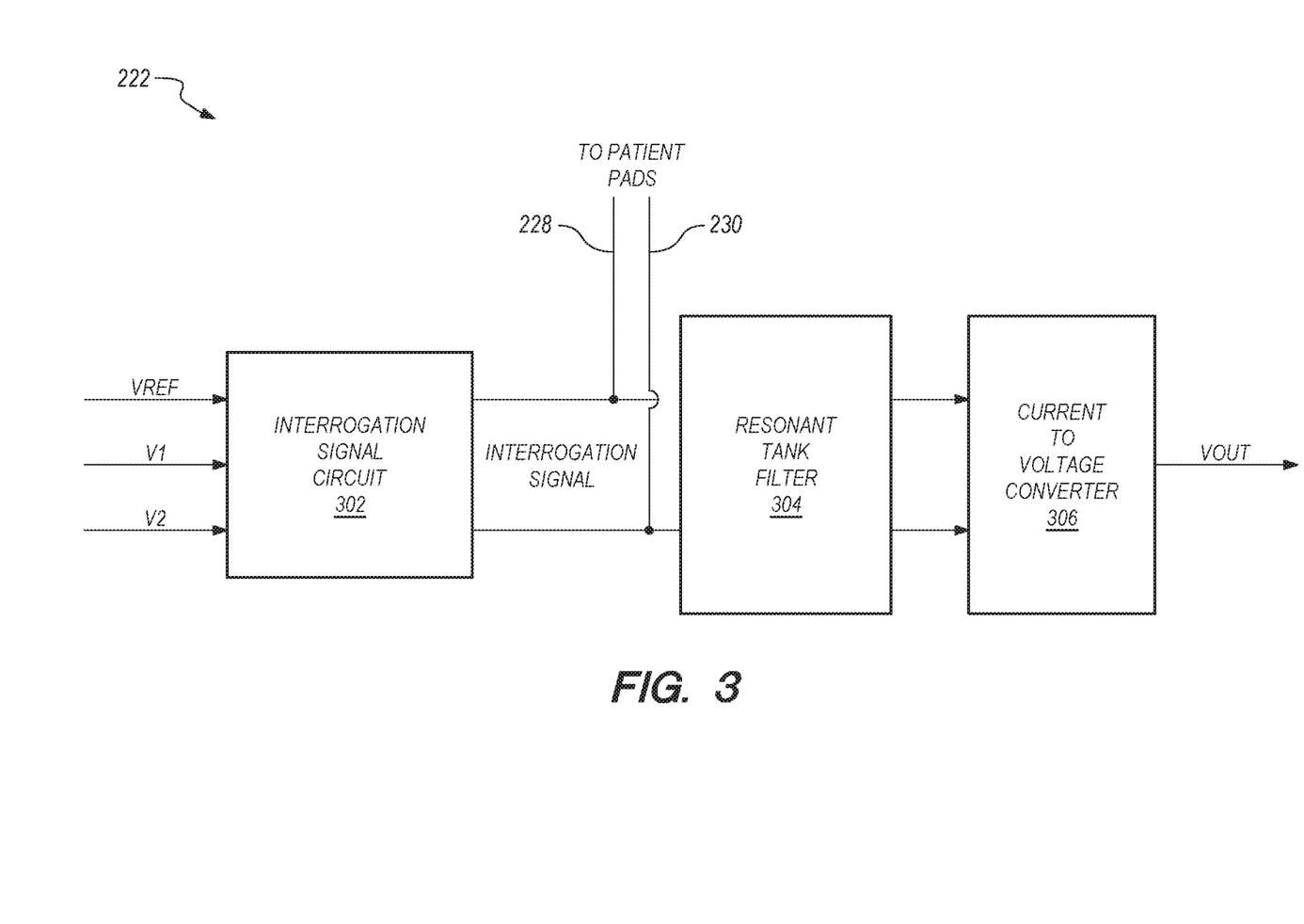
FIG. 3 is a block diagram of an example detection circuit according to the present disclosure.

FIG. 3 is a block diagram of the detection circuit 222 according to the present disclosure. The detection circuit 222 includes an interrogation signal circuit 302, a resonant tank filter 304, and a current-to-voltage converter 306. The interrogation signal circuit 302 is configured to provide an interrogation signal to at least one of the split electrode pads 224 and/or 226 by way of leads 228 and/or 230, respectively. The interrogation signal, in one example, is based on one or more control signals provided to the interrogation signal circuit 302 by the second controller 220.

The resonant tank filter 304 is tuned to resonate at a predetermined frequency and is configured to filter a response signal received from the at least one of the split electrode pads 224 and 226.

The current-to-voltage converter 306 is configured to generate a voltage signal (labeled "Vout" in FIG. 3) based on a current value of the response signal received and filtered by the resonant tank filter 304. The voltage signal generated by the current-to-voltage converter 306 is provided to the second controller 220, which is configured to generate (for example, using an analog-to-digital converter (ADC)) a digital impedance value based on the voltage signal, and provide the digital impedance value to the first controller 202 by way of the isolation circuit 216.

The one or more modulators/demodulators 234 of the isolation circuit 216 are configured to modulate the digital impedance value according to a predetermined type of modulation and communicate the modulated digital impedance value to the first controller 202 by way of the transformer 232. Example types of modulation that can be employed as the predetermined type of modulation include, without limitation, amplitude modulation (AM), phase shift keying (PSK) modulation, frequency modulation (FM), and/or any other suitable type of modulation.

In some examples, the second controller 220 is configured to periodically generate respective digital impedance values based on respective values of the voltage signal received at successive times according to a predetermined time interval. The second controller 220 periodically provides the respective digital impedance values to the first controller 202 by way of the isolation circuit 216 for processing.

The first controller 202 is configured to receive the digital impedance value provided by the second controller 222 and determine whether any action is to be taken based on the received digital impedance value. For example, the first controller 202 may disable delivery of energy (such as energy generated by the HVPS 204) to an active electrode of the electrosurgical instrument 102 based on the received digital impedance value.

The second controller 220 is configured to generate the digital impedance value in a number of ways. For example, the second controller 220 can generate the digital impedance value based on a collective impedance of an interface between the patient P and all of the electrode pads 224 and 226 of the return electrode 108. Alternatively and/or additionally, the second controller 220 can generate the digital impedance value based on relative impedances of respective interfaces between the patient P and the electrode pads 224 and 226 of the return electrode 108.

Figure 4:
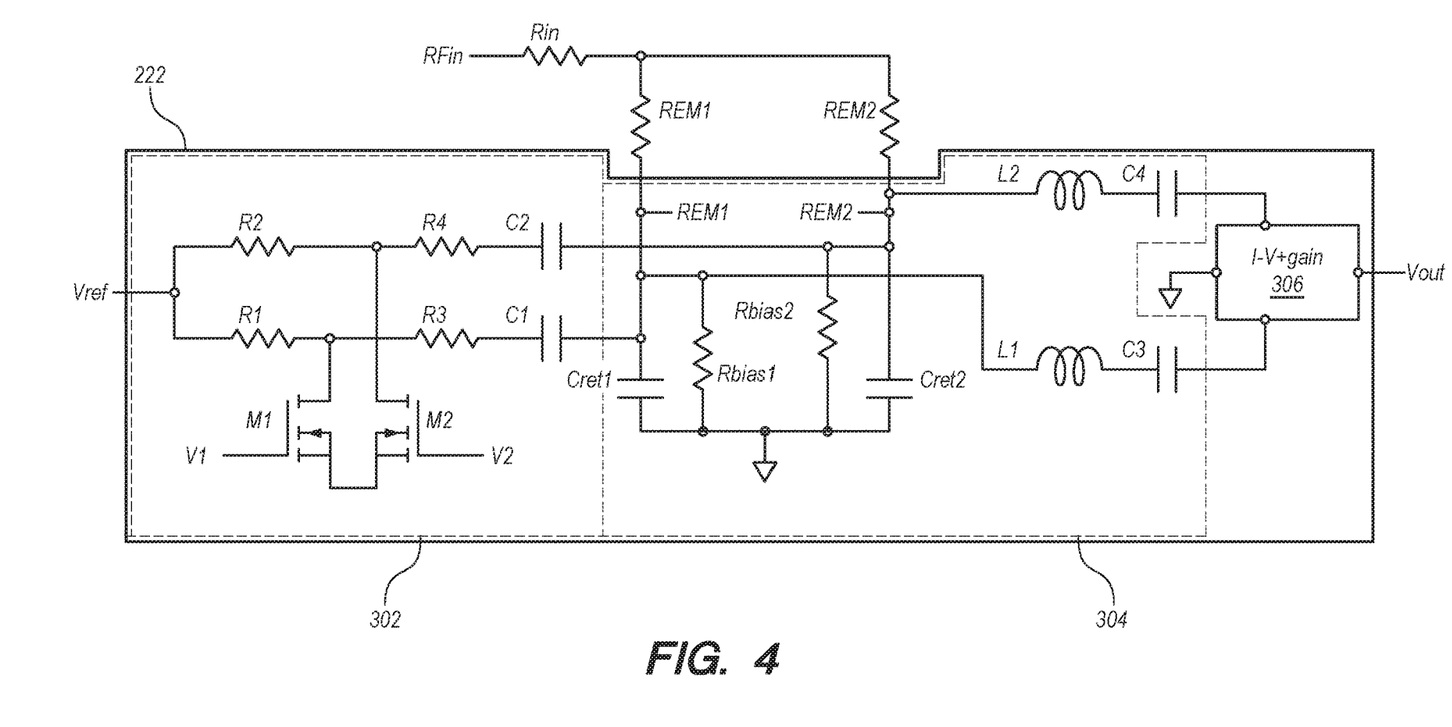
FIG. 4 is a circuit diagram of the example detection circuit of FIG. 3 according to the present disclosure.

FIG. 4 is a circuit diagram of the example detection circuit 222 according to the present disclosure. In particular, FIG. 4 shows example topologies that may be employed as the interrogation signal circuit 302, the resonant tank filter 304, and the current-to-voltage converter 306 of the detection circuit 222.

The interrogation signal circuit 302, in one example, has a current limiting network including at least R1, R2, R3, and R4, which is configured to limit a value of current of the interrogation signal provided to the patient pads 224 and 226. The interrogation signal circuit 302 is provided with a stable voltage reference, Vref, and includes a current limiting network (R1, R2, R3, and R4), and a pair of switches M1 and M2 driven by differential signals V1 and V2, which are provided by the second controller 220 and are set to be 180° out of phase with one another.

The resonant tank filter 304 is set up to resonate at a predetermined frequency (for example, approximately 10 kHz or any frequency that is required for a specific implementation). The resonant tank filter 304 is coupled to the split patient return electrodes REM1 and REM2.

The resonant tank filter 304 includes return energy DC blocking capacitors, Cret1 and Cret2, inductors L1 and L2, fine tuning and offset correction capacitors C3 and C4, and a virtual ground constructed as the input of the current-to-voltage converter 306.

The patient return electrodes are represented in FIG. 4 by terminals REM1 and REM2. Components Rrem1 and Rrem2 shown in FIG. 4 represent the pad-to-patient interface resistances corresponding to the pads 224 and 226, respectively. Component Rin in FIG. 4 represents the body impedance of the patient P.

Although not required in some embodiments, Rbias1 and Rbias2 are configured to drain any undesired DC voltage off of the DC blocking capacitors Cret1 and Cret2, and can also be used for calibration, as described in further detail below.

In this example, the patient return electrodes REM1 and REM2 are excited via the interrogation signal, for example, a 50 µA square, pulsed, or sine wave signal at the resonant frequency. The resulting differential current flowing in the blocking caps Cret1 and Cret2 is proportional to the total circuit impedance. Any common-mode current flow is canceled. Because the only variable is the patient-to-pad interface, the resulting measurement of the differential current flowing in the blocking caps Cret1 and Cret2 is proportional to the impedance of the patient-to-pad interface. The frequency of the interrogation signal may remain fixed or may be continuously adjusted for peak performance or after each activation of energy to the patient P. Further, because the resonant tank filter 304 will filter out all but the fundamental component of the interrogation signal, the interrogation signal may be formed from using any number of waveforms (for example, square waves, pulsed waves, and/or the like).

In some examples, the resonant tank circuit 304 responds to the current of the interrogation signal in a non-linear fashion with respect to the associated patient-to-pad interface resistances. Thus the voltage for very low pad resistances (such as from 0 to 20 ohms) may have a greater change with resistance change than it would with a corresponding resistance change in a higher range of pad resistances. This enables more accurate voltage to relative impedance measurements to be made over a wide range of pad impedances (0 to 300 ohms, for example).

The current-to voltage converter 306 may be implemented by any suitable means of current-to-voltage conversion. For example, the current-to voltage converter 306 may include a set of high speed amplifiers (not shown in FIG. 4) that are configured such that the respective resonant currents (from C4 and C3 in FIG. 4) are fed into the inverting inputs of the amplifiers, feedback from the output of the amplifiers provides the conversion voltage, and a virtual ground is provided to the non-inverting inputs of the amplifiers. The respective voltage signals outputted by the amplifiers can then be summed to provide gain and output as desired. A ground or virtual ground is present at the nodes connecting the two halves of the resonant tank circuit 304 (from C4 and C3).

If the impedance of the two halves of the patient-to-pad interface are unbalanced, interference may occur as a result of the imbalance in the DC blocking capacitors Cret1 and Cret2 during activation of RF energy by the generator 104. This imbalance may be at a much higher frequency (for example, 200 KHz to 450 KHz) than that of the signal exciting the tuned circuit (for example, a 10 kHz) and is therefore greatly attenuated. Further, when RF energy is applied from the patient P through the return energy path, the AC voltage on the DC blocking capacitors Cret1 and Cret2 will be proportional to the current flowing in each capacitor. Therefore, the voltages at REM1 and REM2 may be monitored to measure the resulting current in each of the capacitors Cret1 and Cret2. Once the total circuit impedance is known via the measurement at the resonant frequency (for example, 10 kHz) and the differential impedances are known via the respective activation voltages on the DC blocking capacitors Cret1 and Cret2, the absolute impedance of each section of the patient-to-pad interface can be determined. Thus, if for some reason the impedance of one section of the patient-to-pad interface increases while the impedance of another section of the patient-to-pad interface decreases by the same amount the change can still be detected. Being able to detect such changes can be valuable in predicting patient-to-pad interface changes and maintaining safe system operation.

Figure 5:
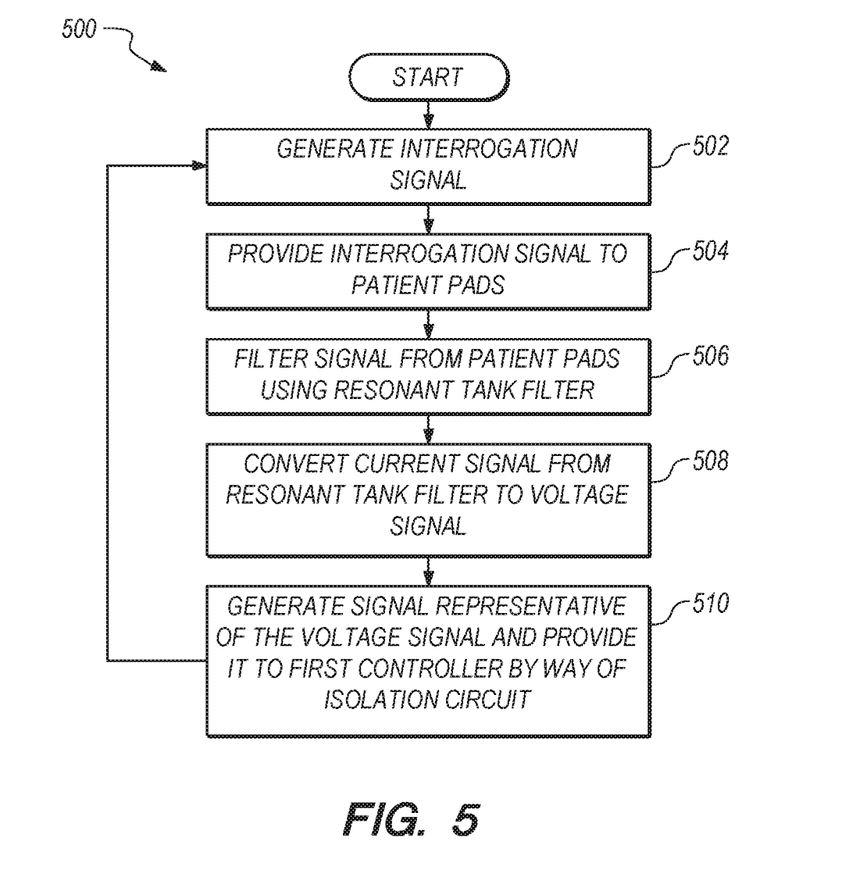
FIG. 5 is a flow chart illustrating an example procedure for return electrode monitoring according to the present disclosure.

FIG. 5 is a flow chart illustrating an example procedure 500 for return electrode monitoring according to the present disclosure. At block 502, an interrogation signal is generated. In one example, the interrogation signal is generated based on one or more control signals (such as the signals carried by terminals V1 and/or V2 depicted in FIGS. 2, 3, and 4) provided to the interrogation signal circuit 302 by the second controller 220. The generating of the interrogation signal can include employing a current limiting network to limit a value of current of the interrogation signal.

At block 504, the interrogation signal generated at block 502 is provided to at least one of the pair of split electrode pads 224 and 226 of the return electrode 108 by way of the leads 228 and/or 230, respectively.

At block 506, a response signal received by the resonant tank filter 304 from the at least one of the split electrode pads 224 and 226 is filtered. In one example, the resonant tank filter 304 is tuned to resonate at a predetermined frequency and the response signal is band-pass filtered according to a frequency band including the predetermined frequency.

At block 508, the current-to-voltage converter 306 generates a voltage signal based on a current value of the response signal filtered at block 506.

At block 510, the second controller 220 generates a signal representative of the voltage signal (such as a digital impedance value) based on the voltage signal, and provides the digital impedance value to the first controller 202 by way of the isolation circuit 216. The second controller 220 is configured to generate the digital impedance value in a number of ways. For example, the second controller 220 can generate the digital impedance value based on a collective impedance of an interface between the patient P and all of the electrode pads 224 and 226 of the return electrode 108. Such a collective impedance may be generally referred to as total patient-to-pad impedance or simply patient-to-pad impedance. Alternatively and/or additionally, the second controller 220 can generate the digital impedance value based on relative impedances of respective interfaces between the patient P and the electrode pads 224 and 226 of the return electrode 108. Other example procedures for generating impedance values based on return electrode monitoring signals are described in U.S. Pat. No. 8,187,263, which is hereby incorporated by reference herein in its entirety.

In one example, the digital impedance value is modulated, by one or more of the modulators/demodulators 234, according to a predetermined type of modulation and the modulated digital impedance value is communicated to the first controller 202 by way of the transformer 232 included in the isolation circuit 216. Example types of modulation that can be employed as the predetermined type of modulation include, without limitation, amplitude modulation (AM), phase shift keying (PSK) modulation, frequency modulation (FM), and/or any other suitable type of modulation.

In another example, the first controller 202 disables the delivery of energy to the active electrode of the electrosurgical instrument 102 based on the digital impedance value provided by the second controller 220 at block 510.

After block 510, the procedures described above with respect to blocks 502, 504, 506, 508, and 510 are repeated for continual and/or periodic return electrode monitoring. For instance, the procedures described above with respect to blocks 502, 504, 506, 508, and 510 can be repeated to periodically generate respective digital impedance values based on respective values of voltage signals successively received at different times according to a predetermined time interval. The respective digital impedance values can be provided to the first controller 202 by way of the isolation circuit 216.

Additionally, although perhaps not shown explicitly in the figures, for patient safety the system and/or procedures herein may further include the following features. A power loss or other subsystem failure will result in data not being transferred to the first controller 202 by the second controller 220. The second controller 220 may include an internal reference voltage and/or a stable voltage feeding power to the second controller 220. Each of these voltages and the Vref signal for the interrogation voltage can be monitored such that, if one of the voltages is out of tolerance it will be detected and the first controller 202 will be alerted. Using the external Vref signal, the second controller 220 power rail, and/or the internal reference voltage, an analog-to-digital converter (ADC) in the second controller 220 may also be monitored.

Furthermore, tank voltage calibration may be obtained using the bias resistors Rbias1 and Rbias2. When the generator 104 is first powered on these resistors may be used to perform calibration before the patient-to-pad interface connector is attached. For proper pad monitoring it may not be required to know the exact absolute impedance of the patient-to-pad interface, so long as an increase in impedance is detectable.

A first type of modulation (such as AM for instance) may be employed to transfer impedance and ratio information to the first controller 202. The data transfer may be group coded and contain redundant coding (for example, a cyclic redundancy check (CRC) code) to maintain data integrity. If the data is corrupted or fails in any other way, the first controller 202 and/or second controller 220 can take appropriate action to prevent or terminate the delivery of RF energy to the instrument 102 until proper data transfer is restored. A second type of modulation (PSK for instance) that does not interfere with the first type of modulation may be employed to communicate control and command information from the first controller 202 to the second controller 220 as needed.

As can be appreciated in view of the above, an improved system and method for return electrode monitoring are provided that address various challenges and are able to communicate information across the isolation boundary between an energy source and a patient. The system and method described herein are improved—in terms of cost-effectiveness, weight, and size—with respect prior REM systems, which require expensive off-the-shelf and custom components that can be heavy and consume a relatively large amount of printed circuit board (PCB) area. The system and method described herein are also improved over prior REM systems in that they, unlike prior REM systems and methods, facilitate the measurement of an individual impedance of an interface between a patient and a single pad of a multiple-pad return electrode (such as a split-pad return electrode, for example), and/or the relative impedances of the respective interfaces between the patient and two or more respective pads of a multiple-pad return electrode.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, causes the one or more processors to perform one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (for example, stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A return electrode monitoring system, comprising:
    an isolation circuit including a transformer having a primary winding and a secondary winding;
    a first controller coupled to the primary winding;
    a second controller coupled to the secondary winding; and
    a detection circuit coupled to the second controller and to a pair of split electrode pads of a return electrode, the detection circuit comprising:
    an interrogation signal circuit configured to provide an interrogation signal to at least one of the pair of split electrode pads,
    a resonant tank filter configured to filter a response signal received from the at least one of the pair of split electrode pads and to output a current value of the response signal,
    which is proportional to an impedance of the at least one of the pair of split electrode pads, and
    a current-to-voltage converter configured to generate a voltage signal based on the current value of the response signal, wherein the first controller is configured to calculate the impedance based on the voltage signal and the current value, wherein the second controller is configured to:
    generate a digital impedance value based on the impedance,
    and provide the digital impedance value to the first controller by way of the isolation circuit.

2. The system of claim 1, wherein the isolation circuit further includes a modulator configured to modulate the digital impedance value according to a predetermined type of modulation and communicate the modulated digital impedance value to the first controller through the transformer.

3. The system of claim 2, wherein the predetermined type of modulation includes at least one of amplitude modulation or phase shift keying modulation.

4. The system of claim 1, wherein the resonant tank filter is tuned to resonate at a predetermined frequency.

5. The system of claim 1, wherein the second controller is further configured to: periodically generate respective digital impedance values based on respective values of the voltage signal successively received at a predetermined time interval; and provide the respective digital impedance values to the first controller through the isolation circuit.

6. The system of claim 1, wherein the first controller is configured to:
    receive the digital impedance value; and
    disable delivery of energy to an active electrode of an electrosurgical instrument based on the received digital impedance value.

7. The system of claim 1, wherein the second controller is configured to generate the digital impedance value based on a collective impedance of an interface between a patient and the pair of split electrode pads of the return electrode.

8. The system of claim 1, wherein the second controller is configured to generate the digital impedance value based on relative impedances of respective interfaces between a patient and the pair of split electrode pads of the return electrode.

9. The system of claim 1, wherein the interrogation signal is based on one or more control signals provided to the interrogation signal circuit by the second controller.

10. The system of claim 9, wherein the interrogation signal circuit includes a current limiting network that limits a value of current of the interrogation signal.

11. A method for monitoring a return electrode, comprising:
generating an interrogation signal at an interrogation signal circuit;
providing the interrogation signal to at least one of a pair of split electrode pads of a return electrode;
filtering a response signal received from the at least one of the pair of split electrode pads;
outputting a current value of the response signal, which is proportional to an impedance of the at least one of the pair of split electrode pads;
generating a voltage signal based on the current value of the response signal;
calculating the impedance based on the current value and the voltage signal;
generating a digital impedance value based on the impedance; and
providing the digital impedance value to a first controller through an isolation circuit.

12. The method of claim 1, further comprising modulating the digital impedance value according to a predetermined type of modulation and communicating the modulated digital impedance value to the first controller through a transformer included in the isolation circuit.

13. The method of claim 12, wherein the predetermined type of modulation includes at least one of amplitude modulation or phase shift keying modulation.

14. The method of claim 11, wherein the filtering of the response signal is performed at a resonant tank filter that is tuned to resonate at a predetermined frequency.

15. The method of claim 11, further comprising:
periodically generating respective digital impedance values based on respective values of the voltage signal successively received at a predetermined time interval; and
providing the respective digital impedance values to the first controller through the isolation circuit.

16. The method of claim 11, further comprising:
disabling delivery of energy to an active electrode of an electrosurgical instrument based on the digital impedance value.

17. The method of claim 11, wherein the generating the digital impedance value includes generating the digital impedance value based on a collective impedance of an interface between a patient and all electrode pads of a split-pad return electrode.

18. The method of claim 11, wherein the generating the digital impedance value includes generating the digital impedance value based on relative impedances of respective interfaces between a patient and a plurality of respective electrode pads of the return electrode.

19. The method of claim 11, wherein the interrogation signal is based on one or more control signals provided to the interrogation signal circuit by a controller.

20. The method of claim 19, wherein the interrogation signal circuit includes a current limiting network that limits a value of current of the interrogation signal.

* * * * *